United States Patent [19]

Mesens

[11] 4,289,783

[45] Sep. 15, 1981

[54] ETOMIDATE-CONTAINING COMPOSITIONS

[75] Inventor: Jean Mesens, Geel, Belgium

[73] Assignee: Janssen Pharmaceutica, N.V., Beerse, Belgium

[21] Appl. No.: 112,671

[22] Filed: Jan. 16, 1980

Related U.S. Application Data

[63] Continuation of Ser. No. 942,236, Sep. 14, 1978, abandoned.

[51] Int. Cl.³ .......................................... A61K 31/415
[52] U.S. Cl. ............................................... 424/273 R
[58] Field of Search .................................. 424/273 R

[56] References Cited

U.S. PATENT DOCUMENTS 3,354,173 11/1967 Godefroi et al. ............... 424/273 B

OTHER PUBLICATIONS

Chemical Abstracts, 84: 99558g and 99559b (1976).
Am. Hospital Formulavy Sev., vol. 2, 1960, p. 72:00, Am. Soc. of Hosp. Pharm.
Holdgroft et al., Br. J. Anaesth.(1976), 48, pp. 199–205.
Doenicke et al., Br. J. Anaesth. (1973), 45, pp. 1097–1104.
Hewdry et al., Anaestheia, 1977, 32, pp. 996–999.
Kay, Br. J. Anaesth. (1976), 48, pp. 207–211.
Janssen et al., Arzhelmittel-Fouschung, 21, 1971, pp. 1234–1243.
Isaac et al., Acta Anaesth. Scandinav, 15, 1971, pp. 141–155.

*Primary Examiner*—Jerome D. Goldberg
*Attorney, Agent, or Firm*—Geoffrey G. Dellenbaugh

[57] ABSTRACT

Improved etomidate-containing compositions for intravenous administration comprising an infusion liquid to which has been added a relatively concentrated solution of an addition salt of etomidate in an ethanolic medium.

12 Claims, No Drawings

ETOMIDATE-CONTAINING COMPOSITIONS

This is a continuation, of application Ser. No. 942,236, filed Sept. 14, 1978, now abandoned.

DESCRIPTION OF THE INVENTION

This invention relates to improved eltomidate-containing compositions, suitable for intravenous administration, a method of preparing the same, and a method of intravenously administering etomidate to a patient in need of same, by the use of such compositions.

Etomidate, being chemically designated as R-(+) ethyl 1-(1-phenylethyl)-1H-imidazole-5-carboxylate is a short-acting hypnotic agent, belonging to the class of allyl 1-(1-phenylalkyl)-1H-imidazole-5-carboxylates which are described in U.S. Pat. No. 3,354,173. More detailed data concerning the hypnotic properties of etomidate are presented in Arzneimittel-Forschung (Drug Research), 21, 1234 (1971).

More recently, etomidate hass been demonstrated to be useful as a maintenance anesthetic which can be used as a substitute for the classical inhalation anaesthetics such as nitrous oxide, halothane and the like. Reports on such utility can be found in Acta anaesth. belg., 28, 107 (1977) and ibid., 23, 115 (1977). It is evident that, in view of its short duration of actior, ectomidate, when used as a maintenance anaesthetic, has to be administered repeatedly or continuously during a certain time interval in order to maintain an effective level of the drug in the patient's blood. This goal can be achieved by administering etomidate in the form of an intravenous infusion at a predetermined rate.

One of the major problems which have been encountered in the course of this development was to find a suitable pharmaceutical composition to be used for the above purpose. It is obvious that such composition must be fully acceptable for the particular, i.e., intravenous way of administration. Moreover the composition should be stable, or, it should be possible to prepare the composition in a convenient and quick manner starting from stable components. Preferably such composition should essentially consist of a solution of the drug in a normal aqueous infusion liquid such as saline, glucose solution or a mixture of saline and glucose solution. None of the previously known compositions completely fulfils the above criteria.

Etomidate is known to be only slightly soluble in neutral aqueous medium. Its solubility is much better in acid medium or in organic solvents such as alcohol and chloroform (see Arzneimittel-Forschung (Drug Research), 21, 1234 (1971). Two types of etomidate-containing compositions which take advantage of the latter properties have been described in the literature.

A first composition, which has been described in Arzneimittel-Forschung (Drug Research) 21, 1234 (1971) comprises a solution of etomidate-base in 60% aqueous propylene glycol. The composition is obviously not acceptable as such for intravenous infusion in view of its very high content of propylene glycol. When diluting the solution with normal infusion liquid some precipitation may occur and this can only be eliminated by vigorous stirring during a rather long time and provided that the final concentration of etomidate in the solution is below about 0.5 mg/ml. Moreover it has been found that etomidate when stored in propylene glycol undergoes to a certain degree transesterification.

Another composition, which has been described in Anaesthesiology and Resuscitation, 106, 1 Berlin-Heidelberg-New York (1977) comprises etomidate sulfate in phosphate buffer to which has been added 4.2% of glucose. The composition is physiologically acceptable but not very stable, etomidate being rapidly hydrolyzed in acidic aqueous medium. An extemporaneous preparation of this composition is not very easy since it requires dissolving a very small quantity of etomidate sulfate in a large volume of buffer. Under these conditions it is rather difficult to ascertain whether the solid has already completely dissolved in the medium. Moreover it has proven difficult to obtain completely dust-free etomidate sulfate which is obviously required for this type of formulation. Concentrated solution of ethomidate sulfate. in aqueous medium, to be further diluted with buffer are not practical because they are not stable for the above-indicated resons.

By the present invention there is provided an etomidate containing composition which is well-suited for intravenous administration, which contains only a minimal amount of organic solvents and which can be prepared very easily and quickly by simply mixing two stable and uncomplicated solutions.

More particularly the present invention provides an etomidate-containing infusion liquid for intravenous administration which comprises a physiologically acceptable infusion liquid to which has been added a concentrated solution of etomidate hydrochloride or hydrobromide in a medium which contains at least 80% by weight of ethanol.

Physiologically acceptable infusion liquids which may advantageously be used for the present purpose are preferably isotonic with blood such as, for example, the standard physiologically acceptable saline and glucose solutions and mixtures of such saline and glucose solutions. Although the hydrobromide salt of etomidate is quite acceptable, the use of the hydrochloride salt is preferred. Besides etomidate hydrochloride or hydrobromide the medium may obviously contain other solvents and/or substances which do not adversely affect the stability and the efficacy of the composition nor its ability to be diluted with physiological liquid.

Although the presence of water enhances the rate of hydrolysis of etomidate in the solution and thus negatively influences the stability of the product it has been found that the medium may contain up to about 20% by weight of water. Lower concentrations of water in the medium, particularly below 5% by weight are however preferred and in an especially preferred embodiment the water-content of the medium is less than 0.5% by weight. In a most preferred embodiment the medium consists of absolute ethanol.

The concentration of etomidate in the composition for intravenous (i.v.) administration may vary within rather wide limits depending on the rate of infusion and the dose requied by the specific circumstances. Concentrations ranging from about 0.05 to about 5 mg etomidate per ml, calculated on etomidate base content, have been found adequate. The concentration of the drug in the ethanolic solution is in general at least 10 times higher than that in the i.v. composition in order to keep the concentration of ethanol in the i.v. composition below physiologically acceptable limits.

By the present invention there is also provided a method of administering etomidate to a patient in need of same by administering thereto an etomidate-containing infusion liquid as described hereinabove.

The invention is further illustrated by the following example which by no way is limiting the scope thereof.

EXAMPLE I

A. Preparation of ampoules containing an ethanolic solution of etomidate-hydrochloride at a concentration of 250 mg etomidate base per 2 ml. (Solution A)

143 g of etomidate hydrochloride (corresponding to 125 g base) are dissolved in absolute ethanol (99.8%) while stirring. The solution is filtered dust-free over a membrane filter of pore size 1.2μ. The solution is further sterilized by filtration over a membrane filter (pore size 0.2μ) and filled into 2 ml ampoules. The latter are saled and autoclaved at 120° C. for 20 minutes.

B. Preparation of etomidate-containing infusion liquid

An etomidate-containing infusion liquid containing 1 mg of etomidate base per ml is prepared by adding 2 ml of solution A to 250 ml of physiological saline or glucose solution. The composition is suitable for intravenous administration to a patient in need of same.

What is claimed is:

1. An etomidate-containing infusion liquid for intravenous administration to provide an anesthetic effect which comprises a physiologically acceptable infusion liquid to which has been added a solution of etomidate hydrochloride or hydrobromide in a medium which contains from 80% to about 99.8% by weight of ethanol to provide an anesthetically effective concentration of at least 0.05 mg/ml of atomidate in the infusion liquid.

2. A method of intravenously administering etomidate to a patient in need of same to provide an anesthetic effect by intravenously administering thereto an effective anesthetic amount of the etomidate-containing infusion liquid as claimed in claim 1.

3. An etomidate-containing infusion liquid for intravenous administration to provide an anesthetic effect which comprises a physiologically acceptable infusion liquid to which has been added a solution of etomidate hydrochloride in a medium which contains from 80% to about 99.8% by weight of ethanol to provide an anesthetically effective concentration of at least 0.05 mg/ml of etomidate in the infusion liquid.

4. A method of intravenously administering etomidate to a patient in need of same to provide an anesthetic effect by intravenously administering thereto an effective anesthetic amount of the etomidate-containing infusion liquid as claimed in claim 3.

5. An etomidate-containing infusion liquid for intravenous administration to provide an anesthetic effect which comprises a physiologically acceptable infusion liquid to which has been added a solution of etomidate hydrochloride or hydrobromide in absolute ethanol to provide an anesthetically effective concentration of at least 0.05 mg/ml of etomidate in the infusion liquid.

6. A method of intravenously administering etomidate to a patient in need of same to provide an anesthetic effect by intravenously administering thereto an effective anesthetic amount of the etomidate-containing infusion liquid as claimed in claim 5.

7. An etomidate-containing infusion liquid for intravenous administration to provide an anesthetic effect which comprises a physiologically acceptable infusion liquid to which has been added a solution of etomidate hydrochloride or hydrobromide in a medium which contains from 80% to about 99.8% by weight of ethanol, to provide a concentration of etomidate base in the infusion liquid of from about 0.05 to about 5 mg per ml.

8. A method of intravenously administering etomidate to a patient in need of same to provide an anesthetic effect by intravenously administering thereto an effective anesthetic amount of the etomidate-containing infusion liquid as claimed in claim 7.

9. An etomidate-containing infusion liquid for intravenous administration to provide an anesthetic effect which comprises a physiologically acceptable infusion liquid to which has been added a solution of etomidate hydrochloride in a medium which contains from 80% to about 99.8% by weight of ethanol, to provide a concentration of etomidate base in the infusion liquid of from about 0.05 to about 5 mg per ml.

10. A method of intravenously administering etomidate to a patient in need of same to provide an anesthetic effect by intravenously administering thereto an effective anesthetic amount of the etomidate-containing infusion liquid as claimed in claim 9.

11. An etomidate-containing infusion liquid for intravenous administration to provide an anesthetic effect which comprises a physiologically acceptable infusion liquid to which has been added a solution of etomidate hydrochloride in absolute ethanol, to provide a concentration of etomidate base in the infusion liquid of from about 0.05 to about 5 mg per ml.

12. A method of intravenously administering etomidate to a patient in need of same to provide an anesthetic effect by intravenously administering thereto an effective anesthetic amount of the etomidate-containing infusion liquid as claimed in claim 11.

* * * * *